United States Patent [19]

Murase et al.

[11] 4,370,060
[45] Jan. 25, 1983

[54] FLAME PHOTOMETRIC DETECTOR ANALYZER

[75] Inventors: Isao Murase; Katsutoshi Hirose, both of Yokosuka; Shoji Yoneya, Fujisawa, all of Japan

[73] Assignee: Nissan Motor Co., Ltd., Yokohama, Japan

[21] Appl. No.: 215,198

[22] Filed: Dec. 10, 1980

[51] Int. Cl.³ ............................................. G01N 21/72
[52] U.S. Cl. ................................................... 356/417
[58] Field of Search ................................ 356/417, 315

[56] References Cited

U.S. PATENT DOCUMENTS

| | | | |
|---|---|---|---|
| 3,489,498 | 1/1970 | Brody et al. | 356/417 |
| 4,099,883 | 7/1978 | Berger et al. | 356/417 |
| 4,111,554 | 9/1978 | Colin et al. | 356/417 X |
| 4,234,257 | 11/1980 | Carter et al. | 356/417 |

FOREIGN PATENT DOCUMENTS

| | | | |
|---|---|---|---|
| 55-62343 | 5/1980 | Japan | 356/417 |
| 1207671 | 10/1970 | United Kingdom | 356/417 |

*Primary Examiner*—F. L. Evans
*Attorney, Agent, or Firm*—Thompson, Birch, Gauthier & Samuels

[57] ABSTRACT

A flame photometric detector analyzer comprises a first conduit through which a fuel gas flows, a fuel gas nozzle connected to the first conduit to be supplied with the fuel gas to form a flame at the tip thereof, a second conduit through which a combustion supporting gas is supplied to the vicinity of the tip of the fuel gas nozzle to assist the combustion of the fuel gas discharged from the nozzle, a third conduit through which a sample gas having a measuring object component is supplied to the flame, a device for controlling the concentration of oxygen contained in the combustion supporting gas to be supplied to the flame within a range from 11.5 to 16%, and a device responsive to photoemission from the measuring object component of the sample gas introduced into the flame, thereby decreasing the effect of interference substances to obtain high accuracy of measurement even though the measuring object is of considerably low concentration.

21 Claims, 4 Drawing Figures

4,370,060

FLAME PHOTOMETRIC DETECTOR ANALYZER

BACKGROUND OF THE INVENTION

This invention relates to improvements in a flame photometric detector analyzer for continuously analyzing a component in a sample gas, and more particularly to the flame photometric detector analyzer which is suitable for continuously analyzing the concentration of sulfur compounds contained in exhaust gases to measure oil consumption of an internal combustion engine.

It has been proposed to judge the characteristics of an internal combustion engine by measuring engine oil consumption. This engine oil consumption measurement is accomplished by determining the $SO_2$ concentration in exhaust gases from the engine since sulfur compound is contained in engine oil. Such $SO_2$ concentration determination is also accomplished by using gas chromatographs, in which the concentration of $SO_2$ only in a certain amount of a sample gas can be determined, but it is impossible to continuously determine the $SO_2$ concentration. As appreciated, engine oil consumption varies with varying engine operating conditions, including acceleration, steady state, and deceleration, and with various engine operating parameters such as intake air temperature and engine coolant temperature. In this connection, in order to precisely judge engine characteristics, it is necessary to continuously measure varying oil consumption, i.e., continuously determine the $SO_2$ concentration in exhaust gases from the engine.

In general, flame photometric detector analyzers are used to continuously measure the concentration of $SO_2$ in the exhaust gases. In these flame photometric detector analyzers, a fuel gas such as $H_2$ gas and a combustion supporting gas (usually, atmospheric air containing about 21% $O_2$) are introduced to a burner or combustion chamber to burn the fuel gas in order to form a flame. Thereafter, a certain amount of sample gas or exhaust gases is introduced into the flame to burn $SO_2$ in the sample gas, upon which the burnt $SO_2$ emits flame light. The flame light is then electrically detected by a photomultiplier tube so that the concentration of $SO_2$ is continuously analyzed.

However, even such flame photometric detector analyzers have encountered the following drawbacks: the abovementioned flame light emitted from the burnt $SO_2$ is greatly affected with or receives interference effect from various gas components or interference substances such as CO, $CO_2$, HC (hydrocarbons), $O_2$ and NO which coexist with $SO_2$ in the exhaust gases from the engine. In this regard, such flame photometric detector analyzers are effective for analyzing high $SO_2$ concentration above $SO_2$ 100 ppm, but not effective for analyzing $SO_2$ concentration in the exhaust gases since the concentration of the exhaust gases is considerably lower.

BRIEF SUMMARY OF THE INVENTION

In view of above, the inventors' attention was directed to the fact that the interference effect due to the above-mentioned interference substances varies with the concentration of oxygen contained in a combustion supporting gas or air supplied to a burner chamber of a flame photometric detector analyzer. Moreover, the inventors have found through many experiments, that the interference effect due to interference substances is very slight when the oxygen concentration of the combustion supporting air is below 16%.

Therefore, the flame photometric detector analyzer according to the present invention is of the type wherein a sample gas whose photoemission is detected is introduced into a flame produced by burning a fuel gas upon supplying the combustion supporting gas, and comprises a device for controlling the concentration of oxygen in the combustion supporting gas to be supplied to the fuel gas within a range of 11.5 to 16%. With this arrangement, the interference effect due to the interference components in the exhaust gas is greatly suppressed and, therefore it becomes possible to accurately analyze the concentration of a measuring object component in the sample gas. Additionally, if the concentration of $SO_2$ in automotive internal combustion engine exhaust gas is continuously measured by the analyzer according to the present invention, it is possible to accurately measure the engine lubricating oil consumption since $SO_2$ originates from a sulfur compound contained in engine lubricating oil.

BRIEF DESCRIPTION OF THE DRAWINGS

The features and advantages of the flame photometric detector analyzer according to the present invention will be more clearly appreciated from the following description taken in conjunction with the accompanying drawings in which like reference numerals designate corresponding parts and elements, and in which.

DETAILED DESCRIPTION OF THE INVENTION

Figure 1:
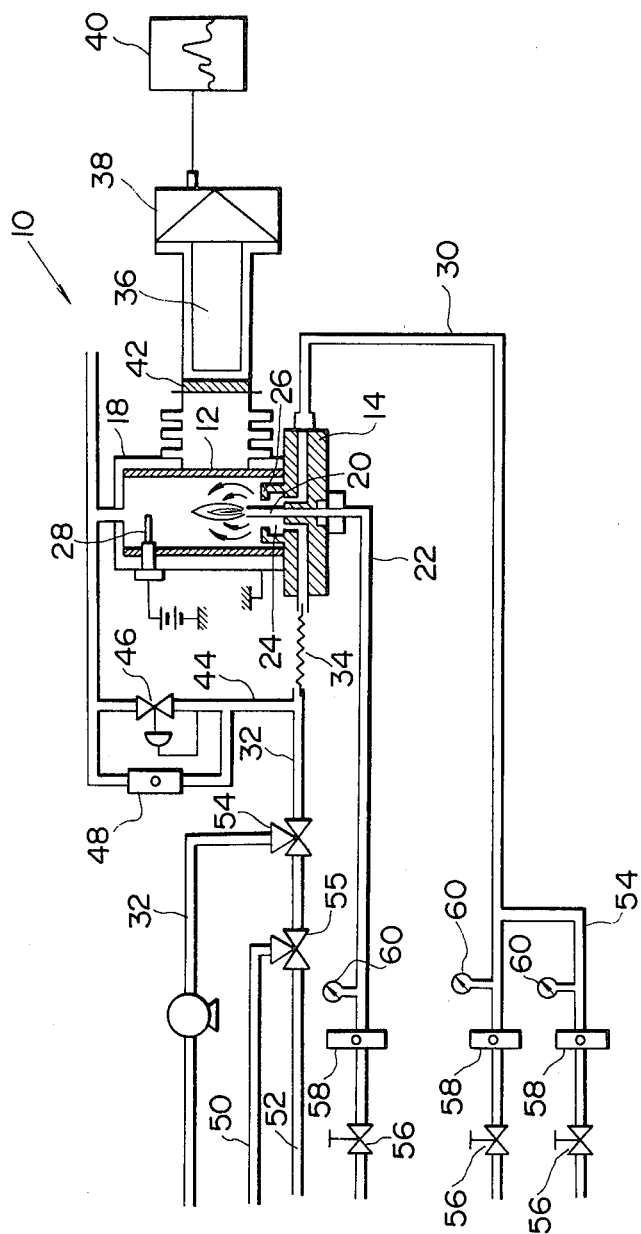
FIG. 1 is a diagrammatic illustration of an embodiment of a flame photometric detector analyzer in accordance with the present invention.

Referring now to FIG. 1 of the drawings, a preferred embodiment of a flame photometric detector analyzer is shown by the reference numeral 10, which analyzer is used, in this instance, for continuously measuring the concentration of $SO_2$ contained in exhaust gases from an internal combustion engine for an automotive vehicle in order to measure engine oil consumption of the engine. The analyzer 10 comprises a heat resisting glass cylinder 12 securely mounted on a base member 14 and defines therein a burner chamber or combustion chamber 16. The glass cylinder 12 is covered with a casing 18 secured to the base member 14.

A burner jet or fuel gas nozzle 20 projects into the combustion chamber 16 from the base member 14 and is connected with a fuel gas supply conduit 22, so that a certain amount of 100% $H_2$ gas supplied through the conduit 22 is ejected from the tip of the fuel gas nozzle 20. An air chamber 24 is defined by an air guide 26 which spacedly surrounds the fuel gas nozzle 20, which air chamber is supplied with a combustion supporting gas (air), so that a certain amount of air is introduced around the tip of the fuel gas nozzle 20 in order that hydrogen gas from the fuel gas nozzle is burned with the air after ignition by an ignitor 28. The air chamber 24 communicates with a combustion supporting gas or air supply conduit 30.

The air chamber 24 also communicates with a sample gas supply conduit 32 via a capillary tube 34 to introduce a certain amount of exhaust gases from the internal combustion engine into the air chamber 24. The flow amount of the sample gas is controlled by the capillary tube 34. The exhaust gas supplied to the air chamber 24 is then introduced into a flame formed at the tip of the fuel gas nozzle 20. When the exhaust gas is introduced into the flame, $SO_2$ in the exhaust gas burns to emit a characteristic flame light having a wave length of about 3940 Angstrom. This flame light is then detected as an electric signal having a certain electric intensity by a photomultiplier tube 36, which electric signal is then amplified by an amplifier 38 and thereafter detected and recorded by a recorder 40. A narrow-band optical filter 42 is provided in front of the photomultiplier tube 36 to improve the detection precision of $SO_2$ by allowing only the light spectrum of $SO_2$ in the exhaust gases to pass therethrough.

A branched conduit 44 is connected to the sample gas supply conduit 32 upstream of the capillary tube 34, and is provided with a constant pressure regulator valve 46 and a flow meter 48. Accordingly, when the pressure within the sample gas supply line 32 upstream of the capillary tube 34 increases above a predetermined level, the constant pressure regulator valve 44 opens to discharge excessive sample gas out of the analyzer 10 to prevent an excessive supply of the sample gas due to the increased pressure differential between the upstream and downstream sides of the capillary tube.

Additionally, first and second standard gas supply conduits 50, 52 are connected via three-way valves 54, 55 to the sample gas supply conduit 32 in order to supply standard gases for adjusting the gain of the amplifier prior to the operation of measuring $SO_2$ in the exhaust gases. A first standard gas for setting the zero point is supplied through the first standard gas supply conduit 50 to the sample gas supply conduit 32, and thereafter a second standard gas for setting the standard point for a measuring object component ($SO_2$) is supplied through the second standard gas supply conduit 52 to the sample gas supply conduit 32. A branched conduit 54 is connected to the air supply conduit 30 to supply 100% $N_2$ gas into the air supply conduit 30 in order to controllably dilute the oxygen concentration in the air supplied to the combustion chamber 16. In FIG. 1, the reference numerals 56 designate valves for controlling the flow amount of fluid; the reference numerals 58 designate flow meters for measuring the flow amount of the fluids; and the reference numerals 60 designate pressure meters for measuring the pressure of the fluids.

It is to be noted that when the sample exhaust gas is introduced into the flame of the fuel gas upon supply of the combustion supporting gas or air in order to measure $SO_2$ concentration in the sample exhaust gas, the flame light emitted from the burned $SO_2$ gas is greatly affected by the interference effect due to so-called interference substances or components which coexist with $SO_2$ in the exhaust gases. This interference effect will be explained with reference to FIG. 2 which was obtained from the experiments by the inventors. The experiments were carried out using five kinds of sample gases (a, b, c, d and e) introduced through the sample gas supply conduit 32 to detect the electric signal intensity (the amplifier output) to be recorded on the recorder 40 upon operation of the detector 10, by varying the $O_2$ concentration in the combustion supporting air supplied through the conduit 30. In this experiment, the sample gas a contains 5 ppm of $SO_2$ in $N_2$ gas; the sample gas b contains 5 ppm of $SO_2$ and 13% of $O_2$; the sample gas c contains 5 ppm of $SO_2$ and 13% of $CO_2$ in $N_2$ gas; the sample gas d contains 5 ppm of $SO_2$ and 5% of CO in $N_2$ gas; and the sample gas e contains 5 ppm of $SO_2$ and 2000 ppm of NO in $N_2$ gas. The output variations indicated by curves a, b, c, d, and e correspond to the sample gases a, b, c, d, and e, respectively.

Figure 2:
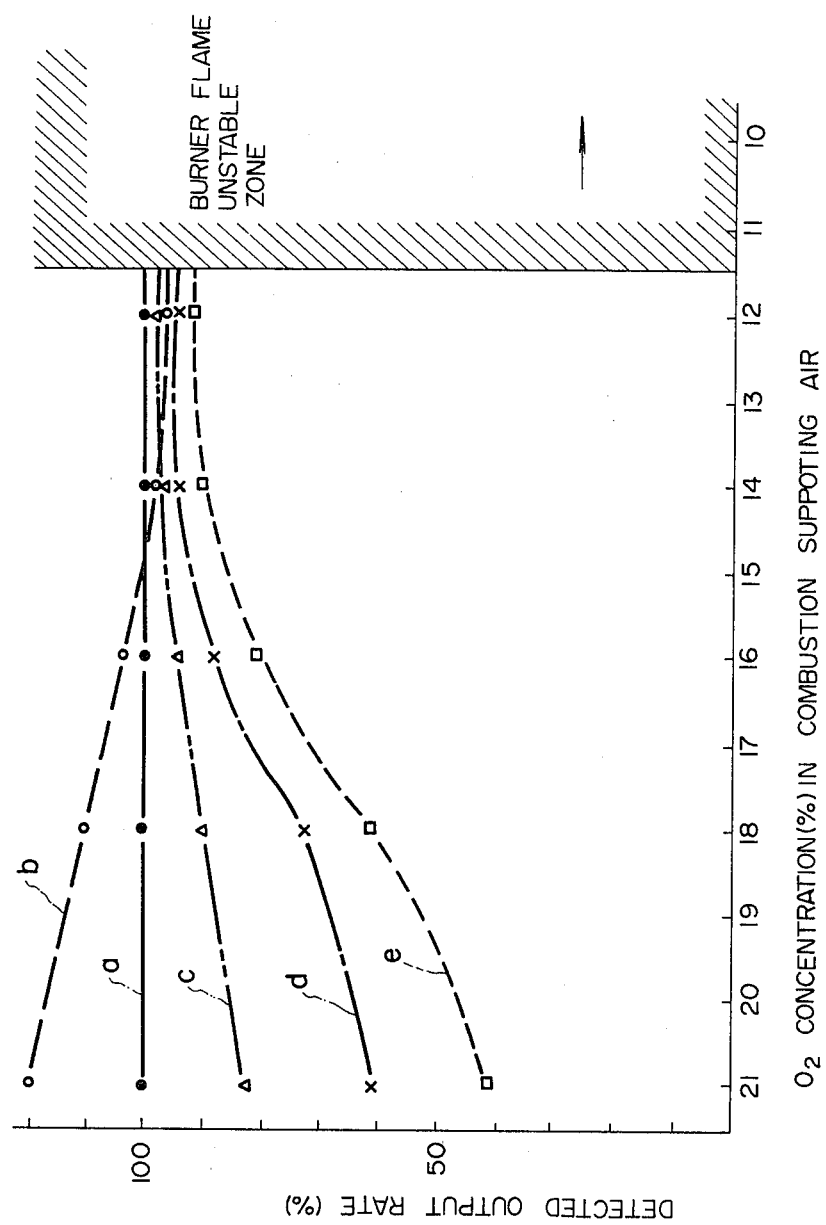
FIG. 2 is a graph showing the basis of selection of an oxygen concentration range in a combustion supporting gas of the present invention.

As apparent from the graph of FIG. 2, if the sample gas contains the interference components such as $O_2$, $CO_2$, CO and NO, the output value from the amplifier of the analyzer considerably deviates from the standard level indicated by the curve a, i.e., greatly receive interference effect from the interference components. Such interference effect from the interference component becomes larger as the oxygen concentration in the combustion supporting air increases to approach the value (about 21%) of atmospheric air. It is to be noted that it was recognized that the deviation from the standard level was small and therefore the interference effect from the interference component was low at an oxygen concentration range up to 16%. It was also recognized that although the above-mentioned deviation of the output value from the amplifier of the analyzer becomes smaller with decreasing oxygen concentration in the combustion supporting air, the flame formed at the tip of the burner jet 20 would become unstable when the oxygen concentration is below 11.5%, i.e., at a burner flame unstable zone shown in FIG. 2.

In view of the above, according to the present invention, the concentration of $O_2$ contained in the combustion supporting air introduced from the conduit 30 to the burner chamber 16 is controlled within a range of 11.5% to 15%. In supplying the thus controlled combustion supporting air, the combustion supporting gas previously diluted within the above-mentioned range may be introduced into the burner chamber 16. However, in order to improve the ignition of fuel gas by the ignitor 28 due to lower oxygen concentration in the combustion supporting air, it is preferable to be able to freely vary the oxygen concentration in the combustion supporting air both at the time of, and after, ignition of the fuel gas.

In this regard, the analyzer 10 shown in FIG. 1 is arranged as follows: Atmospheric air having an oxygen concentration of about 21% is always supplied through the combustion supporting gas supply conduit 30; and 100% $N_2$ gas for diluting the combustion supporting air is selectively introduced through the branched conduit 54 into the conduit 30 so that the oxygen concentration of the combustion supporting air to be supplied to the burner chamber 16 is lowered within the above-mentioned range from 11.5% to 16%, when necessary. With this arrangement, afer ignition of the fuel gas from the tip of the burner jet 20 occurs, the branched conduit 54 is closed to limit the atmospheric air having an oxygen concentration of about 21% into the burner chamber 16 in order to obtain good ignition of the fuel gas. However, after ignition of the fuel gas, the branched conduit 54 is opened to introduce a certain amount of $N_2$ gas into the conduit 30 so that the oxygen concentration of the combustion supporting air to be supplied to the burner chamber 16 is within the above-mentioned range of 11.5% to 16%. It will be understood that by thus controlling the oxygen concentration in the combustion supporting air to the optimum value, the concentration of SO$_2$ in the exhaust gases can be precisely measured without receiving the interference effect from the various interference components contained in the exhaust gases.

Figure 3:
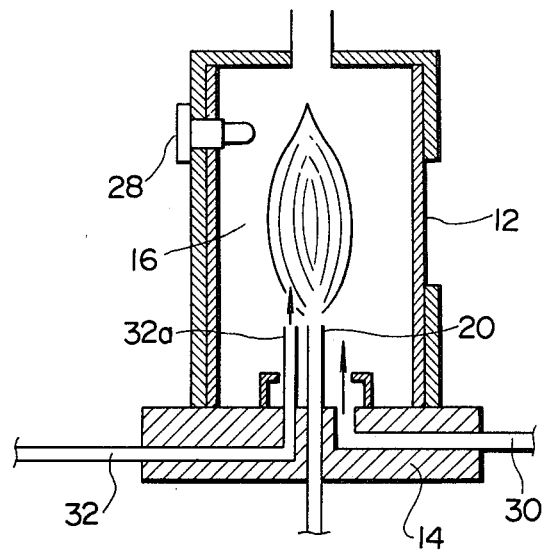
FIG. 3 is a diagrammatic view of an essential part of a modified example of the embodiment of FIG. 1.

FIG. 3 shows a modified example of the embodiment of FIG. 1, in which the sample gas supply conduit 32 extends through the base member 14 into the burner chamber 16 in a manner that the tip 32a of the sample gas conduit reaches the vicinity of the tip of the burner jet 20 in order to directly introduce the sample gas into the flame without premixing with the combustion supporting air.

Figure 4:
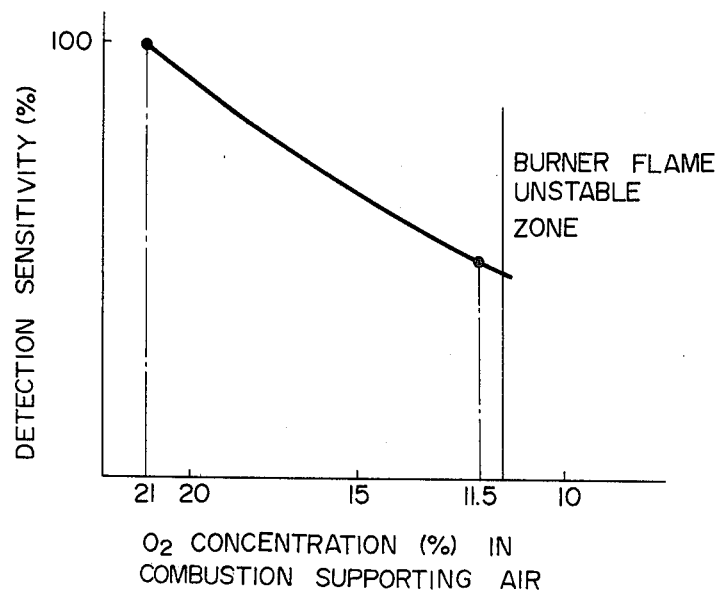
FIG. 4 is a graph illustrating the background on which the example of FIG. 3 is devised, in terms of the oxygen concentration of a combustion supporting gas and detected sensitivity.

The advantages gained by the arrangement of FIG. 3 will be explained hereinafter. If premixing the sample gas with the combustion supporting air was carried out, it was observed that the detecting sensitivity of the detector was lowered with lowering oxygen concentration in the combustion supporting air as shown in the graph of FIG. 4, which, also obtained by the inventors' experiments. This phenomena seems to be based upon the facts that the active flame generation of the fuel gas deteriorates with the lowered oxygen concentration in the combustion supporting air, and that the SO$_2$ concentration of the sample gas is lowered due to premixing the sample gas with the combustion supporting air. On the contrary, with the arrangement of FIG. 3, the sample gas is directly introduced into the flame without premixing with the combustion supporting air, and therefore SO$_2$ concentration in the sample gas is prevented from being decreased to obtain high detecting sensitivity of the detector 10, thereby enabling high accuracy SO$_2$ concentration analysis.

As will be appreciated from the above, according to the present invention, accurate and continuous analysis of SO$_2$ in exhaust gases from an automotive internal combustion engine becomes possible even though the SO$_2$ concentration in the exhaust gas is considerably low, suppressing the interference effect of interference substances coexisting with SO$_2$ in the exhaust gases. Accordingly, engine oil consumption can be accurately measured depending upon the continuously measured SO$_2$ concentration, thereby accurately judging the characteristics of the engine.

While the flame photometric analyzer detector 10 according to the present invention has been shown and described as used for measuring the engine oil consumption, it will be understood that the detector is usuable for other purposes.

What is claimed is:

1. A flame photometric detector analyzer, comprising:
    a first conduit means through which a fuel gas flows;
    a fuel gas nozzle connected to said first conduit means to be supplied with the fuel gas to form a flame at the tip thereof;
    a second conduit means through which a combustion supporting gas is supplied to the vicinity of the tip of said fuel gas nozzle to assist the combustion of the fuel gas discharged from said nozzle;
    a third conduit means through which a sample gas having a measuring object component is supplied to the flame;
    means for controlling the concentration of oxygen contained in said combustion supporting gas to be supplied to the flame within a range of 11.5 to 16%; and
    a photodetector means responsive to photoemission from the measuring object component of the sample gas introduced into the flame.

2. A flame photometric detector analyzer as claimed in claim 1, wherein said controlling means includes means for controllably introducing nitrogen gas into said second conduit means to lower the oxygen concentration of the combustion supporting gas.

3. A flame photometric detector analyzer as claimed in claim 2, wherein said introducing means includes branched conduit means connected to said second conduit means, nitrogen gas flowing in said branched conduit means.

4. A flame photometric detector analyzer as claimed in claim 3, wherein said combustion supporting gas is atmospheric air.

5. A flame photometric detector analyzer as claimed in claim 2, further comprising means for mixing said sample gas with said combustion supporting gas before introduction to the flame formed at the tip of said fuel gas nozzle.

6. A flame photometric detector analyzer as claimed in claim 5, wherein said mixing means includes means defining a mixing chamber around said fuel gas nozzle and communicating with said second and third conduit means so that the sample gas is mixed with the combustion supporting gas therein before introduction to the flame.

7. A flame photometric detector analyzer as claimed in claim 6, wherein said third conduit means includes a capillary tube for restricting the flow amount of the sample gas.

8. A flame photometric detector analyzer as claimed in claim 3, wherein said sample gas is exhaust gas discharged from an internal combustion engine.

9. A flame photometric detector analyzer as claimed in claim 8, wherein said fuel gas is hydrogen gas.

10. A flame photometric detector analyzer as claimed in claim 3, wherein said second conduit means is provided with means for controlling the flow of the combustion supporting gas, and said branched conduit means is provided with means for controlling the flow of nitrogen gas.

11. A flame photometric detector analyzer as claimed in claim 8, wherein said measuring object component of the exhaust gas is a sulfur compound.

12. A flame photometric detector analyzer as claimed in claim 11, wherein said sulfur compound is SO$_2$.

13. A flame photometric detector analyzer as claimed in claim 2, further comprising means for directly introducing the sample gas into the flame formed at the tip of said fuel gas nozzle.

14. A flame photometric detector analyzer as claimed in claim 13, wherein said directly introducing means includes a pipe member connected to said third conduit means, the open tip of said pipe member being positioned in the vicinity of the tip of said fuel gas nozzle.

15. A flame photometric detector analyzer for continuously analyzing the concentration of SO$_2$ contained in exhaust gas from an internal combustion engine, comprising:
    a first conduit means through which hydrogen gas flows;
    a hydrogen gas nozzle connected to said first conduit means to be supplied with hydrogen gas to form a hydrogen flame at the tip thereof;
    a second conduit means through which air is supplied to the vicinity of the tip of said hydrogen gas nozzle to assist the combustion of the hydrogen gas discharged from said nozzle;

a third conduit means through which the exhaust gas is supplied to the flame;

means for controlling the concentration of oxygen of the air flowing in said second conduit means within a range of 11.5 to 16%; and a photodetector means responsive to photoemission from $SO_2$ in the exhaust gas introduced into the flame.

16. An apparatus for measuring engine oil consumption of an internal combustion engine of an automotive vehicle, including a flame photometric detector analyzer for continuously analyzing $SO_2$ concentration in engine exhaust gas originating from a sulfur compound contained in the engine oil, said detector comprising:

a first conduit means through which hydrogen gas flows;

a hydrogen gas nozzle connected to said first conduit means to be supplied with hydrogen gas to form a hydrogen flame at the tip thereof;

a second conduit means through which air is supplied to the vicinity of the tip of said hydrogen gas nozzle to assist the combustion of the hydrogen gas discharged from said nozzle;

a third conduit means through which the exhaust gas is supplied to the flame;

means for controlling the concentration of oxygen of the air flowing in said second conduit means within a range of 11.5 to 16%; and a photodetector means responsive to photoemission from $SO_2$ in the exhaust gas introduced into the flame.

17. A method of continuously analyzing the concentration of a measuring object compound in a sample gas comprising the following steps of:

supplying a fuel gas to a burner jet from which the fuel gas is ejected to form a flame when burned;

supplying a combustion supporting gas to support the burning of the fuel gas;

controlling the concentration of oxygen contained in the combustion supporting gas within a range of 11.5 to 16%, before the combustion supporting gas reaches the fuel gas;

introducing the sample gas into the flame;

detecting the photoemission from the measuring object component in the sample gas introduced into the flame.

18. A method of continuously analyzing the concentration of $SO_2$ in automotive vehicle exhaust gas, comprising the following steps of:

supplying hydrogen gas to a burner jet from which the hydrogen gas is discharged to form a hydrogen flame when burned;

supplying air to support the burning of the hydrogen gas;

mixing nitrogen gas with air so that the oxygen concentration of the air is within a range of 11.5 to 16%, before the air reaches the hydrogen gas;

introducing the exhaust gas into the flame;

detecting the photoemission from $SO_2$ in the exhaust gas introduced into the flame.

19. A method of decreasing the effect of interference substances in a flame photometric detector analyzer of the type wherein a sample gas whose photoemission is detected is introduced into a flame which is produced by burning a fuel gas upon supplying a combustion supporting gas, said method comprising the step of:

controlling the oxygen concentration of the combustion supporting gas within a range from 11.5 to 16%.

20. A method as claimed in claim 19, wherein said oxygen concentration controlling step includes mixing nitrogen gas with the combustion supporting gas to lower the oxygen concentration in the combustion supporting gas, before the combustion supporting gas is supplied to the fuel gas.

21. A method of decreasing the effect of interference substances in a flame photometric detector analyzer of the type wherein automotive engine exhaust gas whose photoemission is detected is introduced into a flame which is produced by burning hydrogen gas upon supply of air, said method comprising the step of:

mixing nitrogen gas with the air so that the oxygen concentration of air is within a range of 11.5 to 16%, before the air is supplied to the hydrogen gas.

* * * * *